(12) United States Patent
Ott

(10) Patent No.: US 7,125,728 B2
(45) Date of Patent: Oct. 24, 2006

(54) DETERMINATION OF PREGNANCY STATUS IN CATTLE AND SHEEP

(75) Inventor: Troy L. Ott, Moscow, ID (US)

(73) Assignee: Idaho Research Foundation, Moscow, ID (US)

( * ) Notice: Subject to any disclaimer, the term of this patent is extended or adjusted under 35 U.S.C. 154(b) by 403 days.

(21) Appl. No.: 10/166,929

(22) Filed: Jun. 10, 2002

(65) Prior Publication Data

US 2002/0192838 A1      Dec. 19, 2002

Related U.S. Application Data

(60) Provisional application No. 60/299,553, filed on Jun. 19, 2001.

(51) Int. Cl.
- *G01N 33/53* (2006.01)
- *G01N 33/50* (2006.01)
- *G01N 33/573* (2006.01)
- *C12Q 1/68* (2006.01)

(52) U.S. Cl. ............................. 436/510; 436/65; 435/6; 435/7.1; 435/7.4

(58) Field of Classification Search .................... 435/6; 436/65, 510

See application file for complete search history.

(56) References Cited

U.S. PATENT DOCUMENTS

| | | | |
|---|---|---|---|
| 3,689,633 A | 9/1972 | Sanae | |
| 4,705,748 A | 11/1987 | Sasser et al. | |
| 4,895,804 A | 1/1990 | Bostwick | |
| 2001/0024799 A1* | 9/2001 | Jordan et al. | 435/7.9 |

FOREIGN PATENT DOCUMENTS

| | | |
|---|---|---|
| CA | 1185176 | 4/1985 |
| WO | WO 00/51520 A3 | 9/2000 |

OTHER PUBLICATIONS

Hicks et al, 2003. Expression of the uterine Mx protein in cyclic and pregnant cows, gilts, and mares. J. Anim. Sci. 81: 1552-1561.*
Johnson et al, 1999. Expression of Interferon Tau Inducible Ubiquitin Cross-Reactive Protein in the Ovine Uterus. Biology of Reproduction, 61: 312-318.*
Zimmerman et al; 2003. Expression of beta hCG and alpha CG mRNA and hCG hormone in human decidual tissue in patients during tubal pregnancy. Molecular Human Reproduction. 9(2): 81-89.*
Kim et al, 2003. Identification of Genes in the Ovine Endometrium regulated by Interferon tau Independent of Signal Transducer and Activator of Transcription 1. Endocrinology 144(12): 5203-5214.*
Alexander et al, 1998. HCG Secretion by Peripheral Mononuclear Cells During Pregnancy. Domestic Animal Endocrinology, vol. 15(5):377-387.*
Short et al, 1992. Biology of Reproduction. 46: 464-469.*
Li et al, 2004. J Dent Res. 83(3): 199-203.*
Yankey et al, 2001. Journal of Endocrinology. 170: R7-R11.*
Walters et al, 2004. Biochimica et Biophysica Acta. 1695: 73-87.*
Bazer et al, 1997. American Journal of Reproductive Immunology. 37: 412-420.*
Zhang et al, 2004. Journal of Leukocyte Biology. 75: 358-372.*
Johnson, GA, et al., "Pregnancy and Interferon-Tau Induce Conjugation of Bovine Ubiquitin Cross-Reactive Protein to Cytosolic Uterine Proteins", Biology of Reproduction, 58:898-904 (1998).
Hansen, TR, et al., "Transient Ubiquitin Cross-Reactive Protein Gene Expression in the Bovine Endometrium", Endocrinology, 138(11):5079-5082 (1997).
Ott, TL, et al., "Effects of the Estrous Cycle and Early Pregnancy on Uterine Expression of Mx Protein in Sheep (*Ovis aries*)", Biology of Reproduction, 59:784-794 (1998).
Spencer, TE, et al, "Differential Effects of Intrauterine and Subcutaneous Administration of Recombinant Ovine Interferon Tau on the Endometrium of Cyclic Ewes", Biology of Reproduction, 61:464-470 (1999).
Leaman, DW and Roberts, RM, "Genes for the Trophoblast Interferons in Sheep, Goat, and Musk Ox and Distribution of Related Genes Among Mammals", Journal of Interferon Research, 12:1-11 (1992).

* cited by examiner

*Primary Examiner*—Gary B. Nickol
*Assistant Examiner*—Zachary C. Howard
(74) *Attorney, Agent, or Firm*—Howard Eisenberg, Esq.

(57) ABSTRACT

A method and kit for determining whether an animal is not pregnant, or is pregnant following a breeding. The level of expression of a pregnancy induced protein is determined in an animal for which pregnancy status information is desired and the level is compared to that of the level in animals that are not pregnant.

11 Claims, 2 Drawing Sheets

DETERMINATION OF PREGNANCY STATUS IN CATTLE AND SHEEP

This application claims the benefit of pending provisional patent application Ser. No. 60/299,553, filed Jun. 19, 2001.

This invention was developed in part with funds under the following Federal Grants: USDA-FAH # IDA02-AHD98. NIH #1 P20 RR 15587-01, and USDA-NRI # 00-35203-9185.

FIELD OF THE INVENTION

The invention relates to methods for determining the pregnancy status of animals. Particularly, the invention relates to methods for determining the pregnancy status of non-ungulates, ungulates, and ruminant animals.

BACKGROUND OF THE INVENTION

In the rearing of livestock, it is very important to accurately determine the pregnancy status of bred animals. In particular, it is the accurate and early identification of failed pregnancy of an animal that has been bred that is economically important. Presently, once an animal is bred, for example a cow, pregnancy status is determined by such methods as palpation, which does not provide an accurate determination of pregnancy status until after 30 days following breeding. Because cattle have an estrous cycle of about 21 days, this means that with presently available methods at least one opportunity for breeding an animal that fails to conceive, the estrus period immediately following the failed breeding, will be missed.

This has important economic consequences for the cattle breeding industry, especially for the dairy industry. Efficient milk production farming requires that cows be successfully bred to become pregnant 80–100 days after calving. Dairy cows, however, have a low fertility rate with artificial insemination, requiring, on average, 2.5 to 3 inseminations per conception. Therefore, a significant need exists for a method by which a dairy farmer may accurately determine that an animal is not pregnant without missing an opportunity to re-breed the animal at the next estrus period following an unsuccessful breeding.

Sasser, U.S. Pat. No. 4,705,748, incorporated herein by reference, discloses a method for determining pregnancy by detecting a protein produced by a conceptus. By this method, cattle were determined to be pregnant as early as day 27 following breeding. Sasser does not disclose the diagnosis of pregnancy prior to the time when a subsequent estrus period will have commenced in non-pregnant cattle and does not disclose an early determination of non-pregnancy.

Maternal recognition of pregnancy in ungulates involves local and systemic gene regulation by the conceptus that results in reduced or altered production of the luteolytic signal, prostaglandin F2α ((PGF2α); Yankey et al., Expression of the antiviral protein Mx in peripheral blood mononuclear cells of pregnant and bred, non-pregnant ewes. Journal of Endocrinology 170, R7–R11 (2001); Bazer et al., Regulation of endometrial responsiveness to estrogen and progesterone by pregnancy recognition signals during the peri-implantation period. In Molecular and Cellular Aspects of Peri-implantation Processes, pp 27–47. Ed S. K. Dey. Springer-Verlag, New York, Inc. (1995)). This is in contrast to pregnancy recognition in primates, which involves a direct luteotrophic effect on the corpus luteum (CL) by conceptus-produced chorionic gonadotropin (Bazer et al. 1995). The signal for maternal recognition in ungulates is the secretion by the conceptus of interferon-tau (IFNτ) during the second and third week of pregnancy (Bazer et al., 1995; Godkin et al., J. Reprod. Fert. 65:141–150(1982)). IFNτ prevents increases in endometrial estrogen and oxytocin receptors, to abrogate oxytocin-induced luteolytic pulses of PGF2α, and maintains CL function (Spencer et al., Endocrinology 136:4932–4944 (1995)).

IFNτ is a member of the Type I IFN family, which also includes IFN α, β, and ω (Samuel, Virology 183:1–11 (1991)), and, more recently, interferon δ (Lefevre, F., et al., Biochimie 80:779–788 (1998). IFNτ signaling through the Type I IFN receptor and Janus Kinase (JAK)—signal transducer and activator of transcription (STAT) signal transduction pathway (Stewart et al., Endocrinology 142:98–107 (2001)) induces a number of genes in the ovine uterus including 2',5' oligoadenylate synthetase (Johnson et al., Biol. Reprod. 64:1392–1399 (2001)), β2-microglobulin (Vallet et al., J. Endocrinol. 130:R1–4 (1991)), IFN regulatory factor 1 (Spencer et al., 1998), ubiquitin cross-reactive protein (Johnson et al., Biol. Reprod. 62:622–627(2000)), and Mx protein (Charleston and Stewart, Gene 137:327–331 (1993); Ott et al., Biol. Reprod. 59:784–794 (1998)). While the functions of many of these proteins in the antiviral response are well characterized, their roles during early pregnancy are not.

Mx proteins are monomeric GTPases, which, depending on the species of animal and type of virus, are potent inhibitors of viral replication (Samuel, Virology 183:1–11 (1991)). The sequences of Mx proteins from various species, including sheep, cattle, pigs, and horses, are publicly available through GenBank and have been assigned GenBank Accession numbers X66093, U88329, M65087, and U55216, respectively. Although the antiviral effects of Mx are generally directed against negative-stranded RNA viruses (e.g. orthormyxovirus), their expression is induced in all cells that possess Type I IFN receptors and has been used to distinguish between bacterial and viral infection (Haller et al., Rev. Sci. Tech. 17:220–230 (1998)). Recently Mx mRNA and protein were shown to be elevated from epithelium (by day 13) to myometrium (by day 15) within the uterine wall in pregnant ewes and levels remained elevated through day 25 (Ott et al., Biol. Reprod. 59:784–794 (1998)). In addition, Mx mRNA levels were elevated in the corpus luteum in response to injections of roIFNτ into the uterine lumen (Spencer et al., Biol Reprod 61:464–470 (1999)).

These results indicated that IFNτ was either: 1) acting directly on all uterine cell types (i.e., epithelial, stromal and myometrial) and on the CL; or 2) inducing substances (cytokines) that have paracrine/endocrine effects on uterine cells and other organs including the ovaries; or 3) affecting components of the uterine mucosal and circulating immune systems which then affect the various uterine cells and CL.

It is impractical, however, to measure the level of Mx protein in uterine tissue as a test for evaluating pregnancy status. Besides being an invasive and time and labor intensive process, the disruption of uterine tissues necessary to determine the uterine levels of Mx would tend to have a deleterious effect on a pregnancy.

A significant need exists for a reliable, reproducible, and non-invasive method for determining pregnancy or lack of pregnancy in domestic livestock.

SUMMARY OF THE INVENTION

It has been discovered that the expression of the genes encoding for several proteins, herein referred to as "pregnancy-induced proteins", including 2',5' oligoadenylate synthetase, β2-microglobulin, IFN regulatory factor 1, ubiquitin cross-reactive protein (also known as "interferon stimulated gene factor 17" ("ISG-17")), and Mx protein, increases significantly in certain animals during the first month of pregnancy. It has further been discovered that the increase in the expression of the pregnancy-induced proteins does not occur in animals that are not pregnant.

In many animals, the increase in expression of the pregnancy induced protein is due to the secretion by the embryo of a hormone, Type I interferon, that is the signal from the embryo to the mother of its existence, referred to as the signal for material recognition of pregnancy. Different type I interferons, including Interferon alpha (IFNα), Interferon beta (IFNβ), Interferon omega (IFNω), Interferon delta (IFNδ), and Interferon tau (IFNτ) are secreted by the embryos of different species. For example, IFNτ is secreted as a pregnancy recognition hormone in ruminants and IFNδ is secreted in swine. In other species, such as horses and other equidae, although the pregnancy-induced protein Mx protein is detectable in the uterus during early pregnancy, to date the secretion by the equine conceptus of a Type I interferon has not been demonstrated. Rather, in equines and other species whose conceptuses do not produce a Type I IFN, it is possible that the uterus produces Type I interferon in response to the presence of the embryo.

In one embodiment, the invention is a method for determining the pregnancy status of an animal. According to this embodiment of the invention, the level of expression of a pregnancy-protein during early pregnancy is determined and compared to the level of the expression of that pregnancy induced protein during the same period in a non-pregnant female animal of the same species. Preferably, the pregnancy induced protein that is determined and compared is a Type I interferon-induced protein. Most preferably, the pregnancy induced protein is Mx protein or ISG-17.

As used herein, the term "pregnancy-induced protein" refers to a protein that is expressed by a maternal gene and which expression is induced in response to the presence of a pregnancy. A pregnancy-induced protein is distinct from a protein that is produced by the conceptus, unless such protein is also expressed by a maternal gene and this maternal expression is induced in response to the presence of a pregnancy.

As used herein, the term "early pregnancy" refers to that time during or following the period of pregnancy recognition signaling in which the level of a pregnancy induced protein is elevated in a pregnant animal compared to a non-pregnant animal of the same species. Although animals that are bred unsuccessfully, that is do not become pregnant, may or may not undergo a period of pregnancy recognition signaling, the term "early pregnancy" is used herein with regards to non-pregnant animals to refer to the period of time in which there would be an early pregnancy if the breeding had been successful. Typically, the period of early pregnancy, as used in relation to the method of the invention, ends at about the end of the first month following conception.

As used herein the "period of pregnancy recognition signaling" refers to that time during which the embryo secretes a protein or hormone, the secretion of which causes recognition by the mother of the existence of the embryo. Although animals that are bred unsuccessfully, that is do not become pregnant, may or may not undergo a period of pregnancy recognition signaling, the term is used herein with regards to non-pregnant animals to refer to the period of time in which, had the breeding been successful, biochemical signaling would be occurring between the conceptus and the uterus.

In accordance with the invention, an animal that is pregnant will exhibit a markedly higher level of expression of one or more pregnancy-induced proteins, such as Mx protein or ISG-17, during early pregnancy, such as during the period of pregnancy recognition signaling, than will a non-pregnant animal of the same species. A non-pregnant animal, whether or not the animal has been bred will exhibit about the baseline level of the pregnancy induced protein expression, including Mx protein, during this period.

In another embodiment, the invention is a kit for determining the reproductive status of an animal of a species in which the conceptus secretes a protein or hormone as a signal for maternal recognition of pregnancy. According to this embodiment of the invention, the kit includes a receptacle for holding a test sample, one or more reagents which when combined with the test sample enable an operator to visually determine the level of one or more pregnancy-induced protein, such as Mx protein or ISG-17, in the test sample, and instructions for determining the level of the protein in the sample. Preferably the kit further contains instructions that enable the operator to determine the pregnancy status of the animal based on the determined level of protein in the sample.

The invention is further illustrated below with reference to Mx protein. One skilled in the art will understand that the disclosure below is applicable to other pregnancy-induced proteins, such as other Type I interferon-induced proteins such as IFNτ induced proteins, including 2',5' oligoadenylate synthetase, β2-microglobulin, IFN regulatory factor 1, and ubiquitin cross-reactive protein, as well as to the illustrated Mx protein. Therefore, in the following disclosure, at the mention of the term "Mx protein", any other pregnancy-induced protein may be substituted.

DETAILED DESCRIPTION OF THE INVENTION

Figure 1:
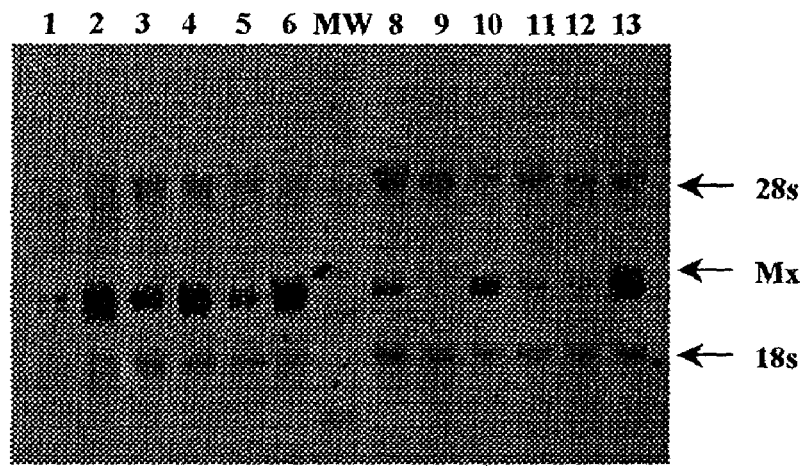
FIG. 1 is a Northern Blot analysis of Mx mRNA from PBMC (peripheral blood mononuclear cells) at day 26 following artificial insemination in ewes. Lanes 1–6 represent pregnant ewes and lanes 8–13 represent non-pregnant ewes. Mx mRNA migrated at ~2.5 kb.

The present invention is applicable to any animal species that secretes increased levels of one or more pregnancy induced proteins during early pregnancy. Preferably, the animal species is one that secretes a Type I interferon as a signal for maternal recognition of pregnancy. Most preferably, the animal species is one that secretes the hormone IFNτ as a signal for maternal recognition of pregnancy. In these animals, the increased levels of Type I interferon, such as IFNτ, induces an increased expression of Mx protein during the period of pregnancy recognition signaling. According to the invention, the lack of an increase in expression of a pregnancy-induced protein, such as Mx protein, in a suitable animal during early pregnancy, preferably the period of time which would encompass the period of pregnancy recognition signaling following a breeding, is a positive indication that the animal is not pregnant. Conversely, a negative result, that is the presence of an increase in expression of the protein during this period is an indication that the animal is pregnant.

In this application, the lack of an increased expression of the pregnancy induced protein, such as Mx protein, is referred to as a positive result whereas the presence of an increased expression of the protein is referred to as a negative result. This terminology, which might at first appear to be contrary to the usual usage of the terms "positive" and "negative" result, is utilized herein because it is the finding of non-pregnancy, rather than of pregnancy, which is of most concern to a farmer or rancher or other person engaged in animal husbandry. If an animal is determined to be pregnant, no additional work is expended to ensure that she is indeed pregnant, outside of watching her to look for signs that the pregnancy has been terminated. In contrast, if an animal is determined to be not pregnant, then she must be further evaluated for the onset of her next estrus and will be bred again. Therefore, it is the finding of non-pregnancy that provides the impetus for additional labor to be expended upon the animal to ensure that she does indeed become pregnant.

As stated above, the invention is applicable to any female animal belonging to a species that produces increased levels of a pregnancy-induced protein during early pregnancy, such as an animal of a species in which a Type I interferon such as IFNτ is the sole signal or one of more than one signal for maternal recognition of pregnancy. Animals suitable for the method of the invention include ungulates and non-hoofed ruminants. The ungulates may be ruminants, such as cattle, sheep, goats, yak, water buffalo, and bison. Included among the ungulate ruminants suitable for the invention are also non-domesticated ungulates such as antelopes, gazelles, elk, reindeer, moose, bighorn sheep, giraffes, and other members of the cattle, sheep, and goat families. Ruminant non-ungulates suitable for the method of the invention include bactrian and dromedary camels and other camellids, such as llamas, alpacas, and vicunas. Ungulate non-ruminants suitable for the invention include domesticated and non-domesticated swine and horses. Animals suitable for the method of the invention include animals other than ungulates and non-hoofed ruminants. For example, it is conceived that primates such as humans, as well as dogs and cats, are suitable for the method of the invention.

In accordance with the method of the invention, during an appropriate time period following breeding, an animal is tested for the presence, or more precisely for the lack of presence, of an increased expression of a pregnancy-induced protein, exemplified hereafter as Mx protein. The test may be performed utilizing any cell in which Mx protein is expressed or in any bodily fluid in which Mx protein is found.

When determining whether an animal has or does not have an increase in expression of Mx protein, a comparison is made to the level of expression in animals that are known to be not pregnant. The comparison may be made, for example, by running a side-by-side comparison of a test sample from an animal that has been bred and which the pregnancy status is uncertain. Alternatively and preferably, the comparison is made by testing a sample from an animal that has been bred and which the pregnancy status is uncertain and comparing the level of Mx protein in the sample to the level of Mx protein known to be present in non-pregnant animals, that is using a historical control.

The invention is illustrated herein with reference to determining the increased expression of Mx protein in peripheral blood mononuclear cells (PBMC). However, any cell in which Mx protein is expressed, including other nucleated cells present in the bloodstream, may be utilized in place of PBMC. Likewise, it is conceived that increased Mx expression in accordance with the invention may be determined by analysis of fluids, such as milk, saliva, urine, or nasal, ocular, or vaginal secretions, or whole blood, plasma, or serum.

Although the period of maternal recognition in most species occurs about the same time, for example at days 12 to 14 following breeding in ewes and days 15 to 18 in cows, the period of embryonic signaling that results in maternal recognition of pregnancy varies somewhat amongst different species. Accordingly, the actual dates following breeding on which the method of the invention may be effectively practiced will vary. For example, the period of maternal recognition of pregnancy signaling in domesticated sheep typically begins about day 11 following breeding and continues to about day 21. In cattle, this period typically begins about day 13 and continues to about day 35.

When comparing the level of Mx protein expression in a test sample to the baseline, (non-pregnant) level of Mx protein expression, typically a doubling or higher in Mx protein expression over the baseline is a negative test, that is the animal is not determined to be not pregnant. Usually, at peak levels of Mx protein expression during the period of pregnancy recognition signaling, a pregnant animal will have levels of Mx protein expression that are up to four or five times, or higher, that of baseline.

In accordance with the invention, the method may be practiced at any time commencing with the onset of the period of signaling until the time that the level of the pregnancy induced protein is no longer elevated in pregnant animals compared to non-pregnant animals of the same species. It is during this time that pregnant animals have an increased expression of Mx protein compared to non-pregnant animals. Thus, in sheep and cattle, a preferred time period for comparing the level of Mx protein expression to determine pregnancy status is between 12 and 30 days following breeding. A more preferred time period is between days 12 and 21 following breeding. A most preferred time period between days 15 and 21, and a most preferred time is on 15 day 18 in cattle and day 15 in sheep.

The level of Mx protein expression may be determined by any method that permits this determination to be made. Suitable methods include detecting the Mx protein itself, such as by ELISA test, an assay based on Mx protein function, or a Western blot. Suitable methods also include detecting increased levels of Mx mRNA, such as by Northern blot, slot blot, or PCR. In a preferred embodiment, the level of Mx protein expression is determined by detecting the level of Mx protein present in a sample by a colorimetric assay based, for example, on the binding of an antibody to the Mx protein, similarly to the methods that are used in human home pregnancy diagnostic kits.

The method of the invention is an accurate, reproducible test that predictably determines that an animal is not pregnant, and may likewise be used to determine that an animal is pregnant. With regards to Mx protein in particular, but not necessarily the other pregnancy induced proteins, the only source of false negative results that would erroneously indicate that the animal is pregnant, that is an increased level of Mx protein expression, is if the animal is suffering from a severe viral infection.

The kit of the invention is preferably based on an enzyme linked assay (ELISA), such as what is known as an "immunometric" or "sandwich" assay. Such an assay involves "sandwiching" a ligand (such as an antigen) with two or more receptor molecules (such as antibodies) which complex with the ligand in a non-interfering manner and at different epitopic sites. Examples of such assays are described in David et al., U.S. Pat. No. 4,486,530. Alternatively, the kit may be based on chemiluminescence assays, enhanced luminescence assays, and radioimmunoassays. In a preferred embodiment, the kit includes a package, which package houses a test surface, such as a slide or multiple test wells, that is bound to an antibody that will bind to an epitope of the protein of interest, such as Mx protein, a container housing a second antibody that will bind to a second epitope of the protein, which second antibody is labeled, a container housing a standard sample having a baseline concentration of the protein, a reagent that when contacted to the labeled second antibody permits the relative amount of the protein present to be visualized, and instructions for use of the kit to determine whether a test sample contains an amount of Mx protein indicative of pregnancy or non-pregnancy status.

The kit of the invention for determining pregnancy status by determining the relative level of a pregnancy induced protein, such as Mx protein, in a test sample compared to a control may be formulated in many different ways, which ways will be apparent to those skilled in the art upon reading the description herein. It is intended that these various formulations of the kit of the invention are included in the invention.

The invention is further described in the following illustrative, non-limiting, examples. The examples describe the method of the invention with reference to Mx protein. However, the method of the invention is applicable to other pregnancy induced proteins.

EXAMPLE 1

Animal Models

Sixty (60) mature, white-faced, ewes from the U.S. Sheep Experiment Station (USSES, Dubois ID) were synchronized and bred either by transcervical or laparoscopic artificial insemination ("AI"). Laparoscopic AI was performed according the procedure disclosed in Stellflug et al., J. Anim. Sci. 79:568–573 (2001). The day of artificial insemination was designated Day 0 (D0) At 26 days after AI (D26), blood (10 ml) was collected by jugular venipuncture into EDTA-containing vacutainer tubes (Sherwood Medical, St. Louis Mo.). PBMC were isolated as described below in Example 2. Pregnancy was determined by assaying serum for pregnancy-specific protein B (PSPB; Biotracking Inc, Moscow Id.) and lambing dates and number of lambs born were recorded.

EXAMPLE 2

PBMC Isolation

Blood was kept on ice until processed. Samples were centrifuged at 300×g for 20 min at 4 C. The buffy coat was removed and resuspended in 0.87% Tris-$NH_4CL$ lysis buffer at a 1 to 5 ratio. Samples were incubated for 5 min at 37° C. and centrifuged at 300×g for 10 min. The supernatant was removed and pellets were washed with 10 ml 1× PBS and centrifuged for 10 min at 300×g. After removal of supernatant, cell pellets were either frozen at −80° C. for protein extraction, or lysed with 2 ml TRIZOL (Life Technologies, Grand Island N.Y.) and stored at −80° C. for RNA extraction.

EXAMPLE 3

RNA Extraction, Northern and Slot-blot Analysis

Total cellular RNA was extracted using TRIZOL according to manufacture's instructions. RNA was quantified by A260:280 ratio. To establish size and number of Mx transcripts in PBMC, RNA (5 µg) was electrophoresed in a 1% agarose/0.615 M formaldehyde gel and transferred to a nylon membrane (Nytran, Schleicher & Schuell, Keene N.H.) by capillary blotting. For quantification of Mx mRNA levels in PBMC, RNA (5 µg) was transferred to a nylon membrane by vacuum filtration (Minifold II, Schleicher & Schuell, Keene N.H.). Blots were probed with a biotin-labeled ovine Mx anti-sense cRNA probe (Ott et al., Biol. Reprod. 59:784–794 (1998)) using the North2South Hybridization kit (Pierce, Rockford Ill.) and chemiluminescent signal was quantified using a Bio-Rad Fluor-S MultiImager system and Quantity One software (Bio-Rad, Hercules Calif.). Slot-blots were stripped and re-probed with an ovine 18s rRNA cRNA probe to correct for variations in RNA loading.

Northern blot analysis, as shown in FIG. 1, detected a single, approximately 2.5 kD, band in PBMC isolated from pregnant and bred, non-pregnant ewes, which agrees with the known size of the ovine uterine Mx cDNA (Charleston and Stewart, Gene 137:327–331(1993); Ott et al., Biol. Reprod. 59:784–794 (1998)).

Figure 2:
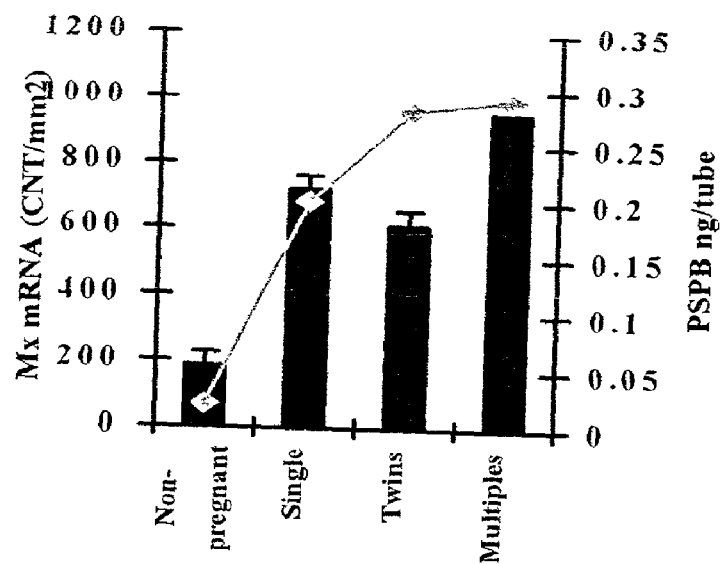
FIG. 2 is a graph showing the results of a slot blot analysis of total cellular RNA isolated from PBMC at day 26 following artificial insemination in ewes. Mx mRNA levels were about 4 fold greater in pregnant verses bred, non-pregnant ewes at D 26 (P<0.01). PSPB (pregnancy-specific protein B) levels (♦) confirmed pregnancy status and were correlated with number of lambs born. (CNTS in FIG. 2 refers to photon counts on a chemiluminscent Northern blot.)

Slot blot analysis, as shown in FIG. 2, of total cellular RNA isolated from PBMC collected at D26 post-AI showed a four-fold increase in Mx mRNA levels in pregnant versus bred, non-pregnant (n=26) ewes ($P<0.01$). In addition, ewes carrying multiples (triplets or quads; n=10) had higher Mx mRNA levels than those carrying singles (n=10) or twins (n=9; $P<0.05$). Results from the PSPB (pregnancy-specific protein B) assay confirmed pregnancy status and, as reported previously, levels of PSPB were correlated with number of lambs born (Willard et al., J. Anim. Sci. 73:960–966 (1995)).

EXAMPLE 4

Temporal Expression of Mx Protein mRNA During Early Pregnancy in Sheep

Figure 3:
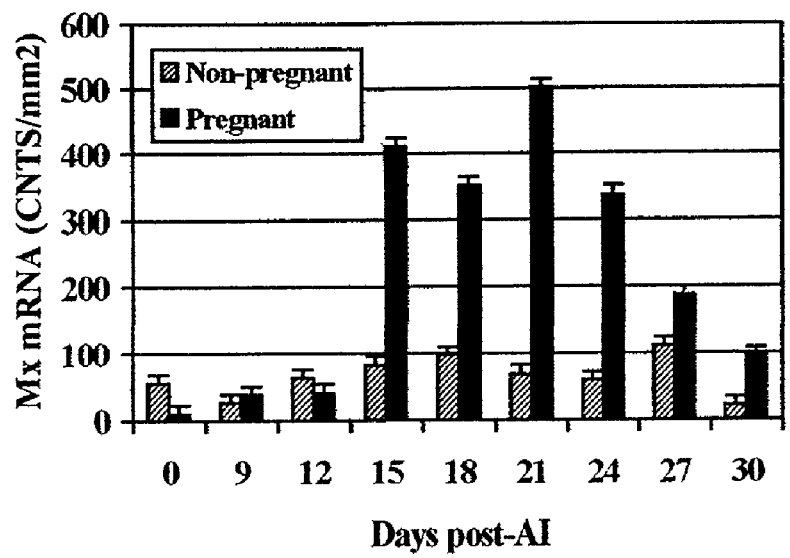
FIG. 3 is a bar graph showing the expression of Mx mRNA in PBMC from artificially inseminated pregnant and non-pregnant ewes from Day 0 to Day 30 following the artificial insemination. (CNTS in FIG. 3 refers to photon counts on a chemiluminscent slot blot.)

A second study examined the temporal expression of Mx mRNA during early pregnancy in sheep, as shown in FIG. 3. Thirty four (34) mature Suffolk ewes were synchronized and bred by laparoscopic AI. Blood (20 ml) was collected by jugular venipuncture at D0, and every three days from D9 to D30, and PBMC were isolated. Pregnancy was confirmed by real-time ultrasonography and PSPB assay at D30. Results shown in FIG. 3 are a representative subset of all ewes and depict results from four pregnant and four bred, non-pregnant ewes during the first 30 days following insemination. This allowed analyzing all replicates on a single blot to eliminate problems associated with signal intensity between blots. Results showed Mx mRNA levels increased in pregnant ewes beginning at D15 (P<0.01). Levels peaked at D21 and gradually declined thereafter. At D30, Mx levels in pregnant ewes remained elevated two-fold compared to bred, non-pregnant ewes (P<0.01).

EXAMPLE 5

Protein Isolation and Western Blot Analysis

Total cellular protein was extracted using M-PER reagent (Pierce, Rockford Ill.), according to manufacturers instructions. Protein concentration of samples was quantified by BCA assay (Pierce, Rockford Ill.) with bovine serum albumen as the standard. Proteins (8 µg/sample) from PBMC isolated from pregnant and bred, non-pregnant ewes at D15 and D18 were separated by 12% SDS-PAGE and electrophoretically transferred to a nitrocellulose membrane (BA83, Schleicher & Schuell, Keene N.H.). Following blocking of non-specific binding sites in 5% non-fat dry milk in Tris-buffered saline and Tween 20 (TBST) for 2 hours at 25° C., membranes were incubated with a 1:1000 dilution of a polyclonal rabbit ovine Mx peptide antiserum (#90618-2; 0.7 µg/ml) at 4° C. overnight. Goat anti-rabbit IgG (0.8 µg/ml) labeled with horseradish perioxidase was used at a 1:200,000 dilution as secondary antibody. Chemiluminescent signal was developed using the West Femto Maximum Sensitivity Substrate (Pierce, Rockford Ill.) and quantified using the Fluor-S MultiImager system and Quantity One software.

Figure 4:
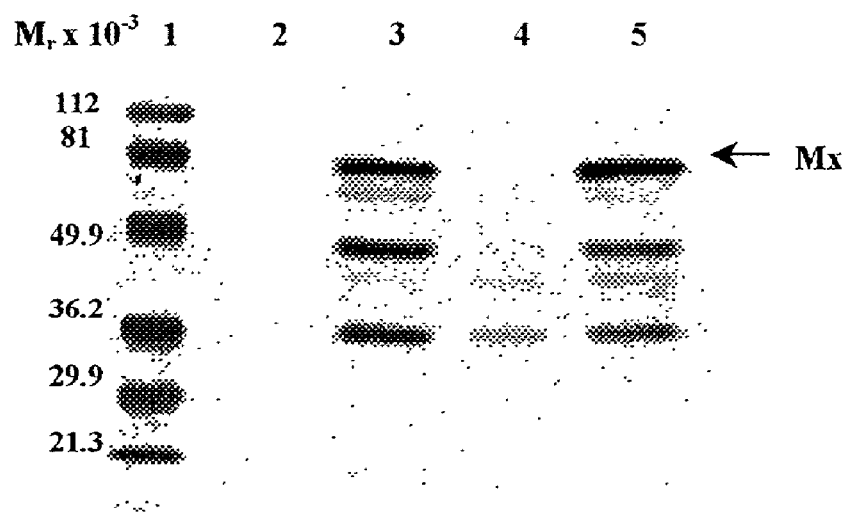
FIG. 4 is a Western Blot analysis of Mx protein expression from PBMC in pregnant and non-pregnant ewes 15 and 18 days following artificial insemination.

As shown in FIG. 4, Mx protein (~75 kDa) was not detected in either D15 or D18 open (non-pregnant) ewes, but was strongly up-regulated in PBMC from pregnant ewes on both days. Two additional bands (~48 and 36 kDa) were detected in PBMC from pregnant ewes.

EXAMPLE 6

Analysis

Chemiluminescent signal was analyzed using GLM procedures of SAS (Version 8.1, SAS Inc, Gary N.C.). The model included, where appropriate, status (pregnant versus bred, non-pregnant), ewe nested within status, day (0, 9, 12, 15, 18, 21, 24, 27, and 30) and appropriate interactions. Error terms in the F test were according to the expectation of mean squares for error. Signal for 18s rRNA was run as a covariate in the model to correct for variations in loading. Results are reported as adjusted Least Squares Means (LSM) and pooled standard errors.

EXAMPLE 7

Cattle

Thirty three dairy cows were bred by artificial insemination and their levels of Mx mRNA were determined by the method described above in Examples 2 and 3. On day 15, levels of Mx mRNA were found to be about the same in cows that were later determined to be pregnant and in cows that were later determined not to be pregnant. On day 18, levels of Mx mRNA were found to be have increased markedly in cows later determined to be pregnant to about three times the level found in cows later determined not to be pregnant.

The results demonstrate a rapid and sustained activation of Mx gene expression in response to pregnancy recognition signaling, and indicate that, in addition to local effects of IFNτ, there is rapid systemic response in sheep and cattle. In addition, Mx expression did not increase in PBMC when pregnancy was not established (bred, non-pregnant animals). These findings are significant because pregnancy recognition signaling by IFNτ was heretofore considered to result solely from local regulation of endometrial gene expression (Stewart et al., Endocrinology 142:98–107 (2001); Johnson et al., Biol. Reprod. 64:1392–1399 (2001); Vallet et al., J. Endocrinol. 130:R1–4 (1991); Spencer et al., Biol. Reprod. 58:1154–1162 (1998); Johnson et al., Biol. Reprod. 62:622–627 (2000); Charleston and Stewart, Gene 137:327–331(1993); Ott et al., Biol. Reprod. 59:784–794 (1998); Spencer et al., Biol. Reprod. 61:464–470 (1999)) and suppression of estrogen and oxytocin receptor expression to abrogate luteolytic pulses of $PGF_{2\alpha}$. The methods and kits of the invention therefore provide new and economically important methods of non-pregnancy, and pregnancy, determinations in livestock.

All articles and patents cited in this application are incorporated herein by reference.

Further modifications, uses, and applications of the invention described herein will be apparent to those skilled in the art. It is intended that such modifications be encompassed in the following claims.

The invention claimed is:

1. A method for determining non-pregnancy status in an animal selected from the group consisting of cattle and sheep, comprising determining the level of extra-uterine expression of a pregnancy-induced protein selected from the group consisting of Mx protein and ubiquitin cross-reactive protein in blood collected from the animal during the period 15 to 27 days following breeding of a ewe or 18 to 30 days following breeding of a cow and comparing the level of expression of said protein in the animal to that of a non-pregnant female animal of the same species, wherein an absence of increase in the level of the expression of the protein in the animal compared to that of the non-pregnant animal indicates that the animal is not pregnant.

2. The method of claim 1 wherein the protein is Mx protein.

3. The method of claim 1 wherein the pregnancy-induced protein is ubiquitin cross-reactive protein.

4. The method of claim 1 wherein the level of expression of the protein is determined by determining the level of mRNA coding for the protein.

5. The method of claim 4 wherein the determination of mRNA is by Northern blot analysis, slot-blot analysis, or polymerase chain reaction.

6. The method of claim 1 wherein the determination of the level of production of the protein is by evaluating the binding of an antibody to the protein or by an assay based on a function of the protein.

7. The method of claim 1 wherein the level of production of the protein is detected by a colorimetric assay.

8. The method of claim 1 wherein the level of expression of the protein is determined by determining the expression of the protein in a peripheral blood mononuclear cell of the animal.

9. The method of claim 1 wherein the comparison is by side-by-side comparison of the level of expression of the protein in the animal and the level of expression in an animal known to be not pregnant.

10. The method of claim 1 wherein the comparing is by using an historical control.

11. The method of claim 1 which is performed during the period between 18 and 21 days after breeding of the ewe or cow.

* * * * *